(12) United States Patent
Hassan et al.

(10) Patent No.: US 11,426,580 B2
(45) Date of Patent: Aug. 30, 2022

(54) SYSTEMS AND METHODS FOR LOW INTENSITY HIGH EFFICIENCY ELECTRICAL STIMULATION

(71) Applicant: HEALTH DISCOVERY LABS LLC, Austin, TX (US)

(72) Inventors: Oussama Hassan, Austin, TX (US); Alaa Hassan, Austin, TX (US)

(73) Assignee: HEALTH DISCOVERY LABS LLC, Austin, TX (US)

( * ) Notice: Subject to any disclaimer, the term of this patent is extended or adjusted under 35 U.S.C. 154(b) by 517 days.

(21) Appl. No.: 15/669,320

(22) Filed: Aug. 4, 2017

(65) Prior Publication Data

US 2018/0043159 A1 Feb. 15, 2018

Related U.S. Application Data

(60) Provisional application No. 62/374,044, filed on Aug. 12, 2016.

(51) Int. Cl.
*A61N 1/36* (2006.01)
*A61N 1/04* (2006.01)

(52) U.S. Cl.
CPC ........ *A61N 1/36031* (2017.08); *A61N 1/0452* (2013.01); *A61N 1/0456* (2013.01); *A61N 1/0476* (2013.01); *A61N 1/0492* (2013.01); *A61N 1/36003* (2013.01)

(58) Field of Classification Search
CPC ................................................. A61N 1/36031
See application file for complete search history.

(56) References Cited

U.S. PATENT DOCUMENTS

| | | | |
|---|---|---|---|
| 6,132,386 A | 10/2000 | Gozani et al. | |
| 6,301,500 B1 | 10/2001 | Van Herk et al. | |
| 6,413,782 B1 | 7/2002 | Parce et al. | |
| 7,720,548 B2 | 5/2010 | King | |
| 7,749,171 B2 | 7/2010 | Gozani et al. | |
| 8,140,165 B2 | 3/2012 | Buhlmann et al. | |
| 8,948,876 B2 | 2/2015 | Gozani et al. | |
| 9,259,164 B2 | 2/2016 | Fadem | |
| 9,474,898 B2 | 10/2016 | Gozani et al. | |
| 9,656,070 B2 | 5/2017 | Gozani et al. | |
| 9,675,801 B2 | 6/2017 | Kong et al. | |
| 2010/0004715 A1* | 1/2010 | Fahey ................ | A61N 1/0456 607/48 |

(Continued)

OTHER PUBLICATIONS

Palmieri et al., The Hoffman Reflex: Methodologic Considerations and Applications for Use in Sports Medicine and Athletic Training Research, Journal of Athletic Training, 2004, 39(3): 268-277. (Year: 2004).*

(Continued)

*Primary Examiner* — Rex R Holmes
*Assistant Examiner* — Jennifer L Ghand
(74) *Attorney, Agent, or Firm* — Pierson Intellectual Property LLC

(57) ABSTRACT

Examples of the present disclosure are related to devices in the field of transcutaneous electrical nerve stimulation and neuromuscular electrical stimulation. More specifically, embodiments are related to devices that are configured to automatically detect the stimulation intensity range and the motor point to generate a high efficiency, low intensity electrical stimulation treatment.

7 Claims, 9 Drawing Sheets

(56) References Cited

U.S. PATENT DOCUMENTS

| | | | |
|---|---|---|---|
| 2010/0087903 A1 | 4/2010 | Van Herk et al. | |
| 2011/0230782 A1* | 9/2011 | Bartol | A61B 5/0488 600/546 |
| 2011/0237974 A1* | 9/2011 | Bartol | A61B 5/0488 600/554 |
| 2013/0030277 A1* | 1/2013 | Fahey | A61B 5/0492 600/384 |
| 2015/0182752 A1 | 7/2015 | Buhlmann et al. | |

OTHER PUBLICATIONS

Tanino et al., M wave and H-reflex of soleus muscle before and after electrical muscle stimulation in healthy subjects, Electromyography Clinical Neurophysiology Journal, 2003, 43, 381-384. (Year: 2003).*

* cited by examiner

INTENSITY RANGE

SYSTEMS AND METHODS FOR LOW INTENSITY HIGH EFFICIENCY ELECTRICAL STIMULATION

CROSS-REFERENCE TO RELATED APPLICATIONS

This application claims a benefit of priority under 35 U.S.C. § 119 to Provisional Application No. 62/374,044 filed on 12 Aug. 2016, which is fully incorporated herein by reference in their entirety.

BACKGROUND INFORMATION

Field of the Disclosure

Examples of the present disclosure are related to devices in the field of transcutaneous electrical nerve stimulation and neuromuscular electrical stimulation. More specifically, embodiments are related to devices that are configured to optimize stimulating electrical pulses characteristics and to detect a motor point based on bioelectrical feedback.

Background

Medical rehabilitation is a branch of medicine that aims to enhance and restore functional ability and quality of life to those with physical impairments of disabilities or chronic illnesses. One form of medical rehabilitation is electrical muscle stimulation (EMS), which is the elicitation of muscle contraction using electrical pulses. The pulses are generated by a device and delivered through electrodes placed on the skin in direct proximity to the muscles to be stimulated. The pulses received from the device mimic the action potential received from the body's central nervous system that cause muscle contraction.

Conventional devices instruct users to place electrode patches over a motor point where muscle contraction is desired, and instruct users to determine the desired treatment intensity range. Due to variations in human anatomy, it is difficult to determine the exact location of the motor point. It is also difficult to determine the desired stimulus intensity required at a motor point to cause muscle contraction for different patients. Additionally, placing electrode patches further away from the motor point will require higher stimulus intensity to contract the associated muscle. This may result in uncomfortable, painful, and less efficient treatment.

Accordingly, needs exist for more effective and efficient systems and methods to automatically determine a location of a motor point for a patient, and determine the most efficient stimulus characteristics to generate muscle contraction at the targeted muscle organ, which may generate a higher efficiency-lower intensity electrical muscle stimulation.

SUMMARY

Embodiments are related to devices in the field of transcutaneous electrical nerve stimulation (TENS) and neuromuscular electrical stimulation (NMES). Embodiments may be configured to optimize electrical pulse characteristics based on bioelectrical feedback such as H-reflex, M-wave or any other bodily measured reflexes, and localize the location of the most favorable electrode set which could be associated with a motor point where a physiological effect, such as muscle contraction, may be effectively induced. In embodiments, a motor point may be a point at which a motor nerve enters a muscle or defined as any point on the skin over a muscle at which electrical stimulation causes most efficient contraction of the muscle.

Such embodiments may determine a minimal level of electrical pulse amplitude desired to induce contraction of the target muscle. A muscle contraction will be more effective if electrical stimulation is applied over the motor point and upon recruitment of a sensory volley. The sensory volley will activate the central nervous system and consequently generate central torque. Recruitment of the sensory volley is possible by applying electrical stimulus at the motor point. Such an embodiment may still determine a minimal amount of stimulus intensity desired to induce peripheral muscle activation without the contribution of the sensory volley. Therefore, embodiments may activate a sensory volley to enhance neuromuscular function for rehabilitation and functional electrical stimulation, which may lead to physiological recruitment of muscle fibers and less painful electrical stimulation than conventional alternatives.

In our description, variations in the electric stimulus characteristics may include any variation in pulse amplitude, frequency, ramp up time, ramp down time, pulse width, duty cycle, symmetrical or asymmetrical pulses, or any other characteristics.

In our description, a motor point is not restricted to the clinical/anatomical definition of a motor point. A motor point could represent any location near or in close proximity to the clinical/anatomical motor point where the best desired response is recorded.

Embodiments may be a wearable or non-wearable device that include an electrical stimulator (ES) (or a stimulus intensity regulator, regulating electrical pulses), electrical measurement system such as an electromyography (EMG) device (measuring bioelectrical feedback), sensing and stimulating set of electrodes, the set of electrodes may be made into a multitude set of electrodes such as an array of electrode sets where each set of electrodes could be individually selected, and a control unit. A control unit may be configured to control and configure the operation of the ES, EMG, and store and analyze data in order to elicit tingling sensation and/or muscle contraction using electrical discharges.

The electrical stimulator may be an electrical pulse generator configured to generate electrical pulses with different characteristics such as different current intensities, voltage amplitudes, ramp up/down time, pulse width, pulse frequency, pulse phase, duty cycle, pulse edge slopes (such as rise and fall time), symmetrical or asymmetrical pulses, monophasic or biphasic pulses or any other characteristics, and deliver the electrical discharges to a user via a set of electrodes.

The electrical stimulator may be configured to send electrical pulses to cause an increasing stimulus intensity starting at a minimal intensity level through a set of electrodes or an array of electrode sets positioned on multiple locations over the treatment area of the user. The electrical stimulator may operate within a range of amplitude levels and/or by changing the pulse characteristics. After each stimulus, the EMG device will scan for H-reflex and M-wave signals, then controller unit determines stimulus amplitude ranges based on the physiological response of the sensory volley and motor nerve respectively. Consequently, the device will determine optimal stimulation window ranges and/or a motor point location by analyzing the captured data.

The electrode sets may be cutaneous electrode patches that are configured to transmit and/or receive electrical signals. In embodiments, a first set of electrode patches may be configured to transmit pulses or waveforms onto skin of a user (called stimulating pulses), and a second set of electrode patches may be configured to sense bioelectrical feedback (called sensing electrodes or EMG electrodes). The first set of electrode patches and second set of electrode patches may be positioned in close proximity to each other. In a different embodiment, the set of electrode patches may be configured to transmit pulses or waveforms onto the skin of a user, and then switch in function to sense bioelectrical feedback (same electrode set has ES and EMG functions).

The electrical measurement system (e.g. electromyography sensor) may be a device configured to measure bioelectrical feedback such as electrical activity of muscle cells when these cells are electrically and/or neurologically (physiologically) activated. The electrical measurement system sensor may be coupled to multiple electrode patches that are spread and placed over muscle mass on multiple locations. The electrical stimulator may sweep the stimulation by varying the electrical pulse characteristics causing an increase of the stimulus intensity until the electrical measurement system sensor detects an effective response from the target organ such as a muscle. An effective first response from the muscle may be based on an H-reflex response, which is a reflectory reaction of muscles after electrical stimulation of sensory afferent fibers. An effective second response could be an M-wave which is a reflectory reaction of muscles after electrical stimulation of the efferent motor nerve.

Responsive to determining an effective response from the muscle, a control unit may be configured to save the data associated with the transmitted stimulus from the ES and to save data associated with the received signal from the EMG. Furthermore, the control unit may be configured to analyze and process captured data. This process may be repeated for a number of different electrode sets.

The control unit may be configured to analyze the recorded data. Electrode set associated with the minimal pulse intensity and leading to the generation of the first physiological response H-reflex or M-wave will be selected as the electrode set positioned over the most favorable location or in near proximity of the motor point. Furthermore, the control unit may be configured to analyze the H-reflex and M-wave relationship to identify the target stimulus intensity range windows. Five different ranges may be identified: A first range labeled as minimal sensation range window where $H \approx 0$ and $M \approx 0$, a second range labeled as transcutaneous electrical nerve stimulation (TENS) range window where $H > 0$ and $M \approx 0$; A third range labeled as optimal intensity range window where $H \geq M$ and $M > 0$; a forth range labeled as forceful contraction range window where $M \geq H$ and $H > 0$, and a fifth range labeled as plateau phase range window where $H \approx 0$ and $M > H$. The ranges of interest will be the TENS range, optimal intensity range, and the forceful contraction range.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
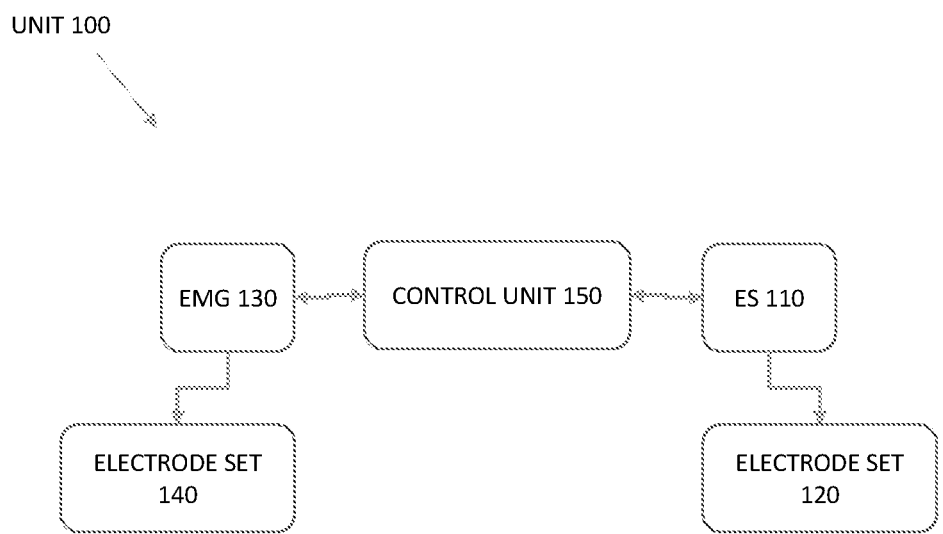
FIG. 1 depicts a wearable or non-wearable device to apply various stimulus range windows using bioelectrical feedback, according to an embodiment.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure. Attached algorithms demonstrate one potential approach to determine the intensity range windows and the motor point location.

DETAILED DESCRIPTION

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Embodiments disclose devices that are configured to optimize electrical pulse characteristics to detect various stimulating windows and determine a motor point to generate tingling sensation and/or muscle contraction, based on bioelectrical feedback such as H-reflex and M-wave.

FIG. 1 depicts a wearable or non-wearable device 100 including an electrical stimulator (ES) 110, first electrode set 120, an electrical measurement system represented as an electromyography (EMG) sensor 130, second electrode set 140, and a control unit 150. Device 100 may be integrated into one enclosure or electronic embodiment. Device 100 may be configured to detect various stimulating windows based on H-reflex and M-wave.

Electrical stimulator 110 may be a device that produces electrical pulses with characteristics related to current intensities, voltage amplitudes, ramp up/down time, pulse width, pulse frequency, pulse phase, duty cycle, pulse edge slopes (such as rise and fall time), symmetrical or asymmetrical pulses, monophasic or biphasic pulses or any other characteristics. Electrical stimulator 110 may be configured based on a signal received from the control unit 150 that configures the characteristics of the electrical pulses. In embodiments, electrical stimulator 110 may be configured to generate a low-amplitude-wide-pulse-high-frequency stimulus or any other stimulus to activate an afferent sensory volley or to generate a conventional electrical pulse to activate the motor nerve. Electrical stimulator 110 may be configured to stimulate underlying nerve fibers via electrode set 120, which transmit the generated pulses onto the targeted location.

First electrode set 120 may be configured to transmit electrical pulses generated by electrical stimulator 110. Electrode set 120 and electrode set 140 could be joined in one single unit or could be two independent units.

Electromyography sensor 130 may be a device that is configured to detect the electrical potential generated by muscle cells when these cells are electrically or voluntarily activated. Electromyography sensor 130 may be coupled with a second electrode set 140 that is placed over muscle mass. Electrical stimulator 110 may be configured to sweep the stimulation by varying the electrical pulse characteristics such as increasing the stimulus intensity until electromyography sensor 130 detects, via second electrode set 140, an effective response from the target muscle or organ. When determining an effective response from the muscle, control unit 150 may be configured to save the data associated with the corresponding transmitted stimulus from the electrical stimulator that caused the effective response from the target muscle or organ.

In embodiments, electromyography sensor 130 may be configured based on a signal received from control unit 150 to determine electrical muscle activity at a predetermined time delay after the pulse stimulus is transmitted from electrical stimulator 110. The predetermined time delay of the muscle activity may be around 5 milliseconds or 25 milliseconds (or any variation of this time), wherein an H-reflex value may be determined around 25 ms after the transmitted stimulus from electrical stimulator 110 and an M-wave may be determined around 5 ms after the transmitted stimulus from electrical stimulator 110. For example, at low intensity, electromyography sensor 130 may determine an H-reflex 25 ms after the stimulus is transmitted from electrical stimulator 110 via first electrode set 120.

Second electrode set 140 may be configured to determine data associated with muscle response to stimulus transmitted via first electrode set 120, such as data associated with an H-reflex or an M-wave. For example, second electrode set 140 may be positioned over muscle belly. Electrode set 140 and electrode set 120 could be joined in one single unit or could be two independent units.

In embodiments, the positioning of second electrode set 140 may be proximate to the positioning of first electrode set 120, wherein first electrode set 120 may transmit a pulse or waveform onto a targeted area of a user and second electrode set 140 may receive the bioelectrical feedback to the transmitted stimulus. First electrode set 120 and second electrode set 140 could be embedded in one assembly unit or could be in two separate assembly units. In a different embodiment, an electrode set may be configured to transmit pulses or waveforms onto targeted area of a user then switch in function to sense bioelectrical feedback (the same electrodes have ES and EMG functions).

Control unit 150 may be a hardware processing device configured to control electrical stimulator (ES) 110 and electromyography sensor (EMG) 130. Control unit 150 may include a processing device and memory. The processing device can include memory, e.g., read only memory (ROM) and random access memory (RAM), storing processor-executable instructions and one or more processors that execute the processor-executable instructions. In embodiments where the processing device includes two or more processors, the processors may operate in a parallel or distributed manner. The memory device may be a device configured to store data generated or received by control unit 150. The memory device may include, but is not limited to a hard disc drive, an optical disc drive, and/or a flash memory drive.

In embodiments, control unit 150 may be able to control the entirety of the pulse characteristics including but not limited to current intensities, voltage amplitudes, ramp up/down time, pulse width, pulse frequency, pulse phase, duty cycle, pulse edge slopes (such as rise and fall time), symmetrical or asymmetrical pulses, monophasic or biphasic pulses transmitted by electrical stimulator 110. Additionally, control unit 150 may be configured to determine the preset time delay since when the pulse stimulus generated by the electrical stimulator 110 is transmitted until when electromyography sensor 130 detects and reads the muscle response as reflected by an H-reflex or M-wave. Responsive to determining the H-reflex and/or M-wave, control unit 150 could be configured to detect different target stimulus windows. Three major different target ranges may be identified as: A. ("TENS range" window) H>0 and M≈0; B. ("Optimal intensity range" window) H≧M and M>0; C. ("Forceful contraction range" window) H>0 and M≧H.

Responsive to scanning for H-reflex and M-wave, electrical stimulator unit 110 may generate pulses of increasing amplitude (or of any variation in the electrical pulse characteristics) until electromyography sensor 130 detects an H-reflex. The first stimulus level leading to the detection of the H-reflex will be recorded as the "Minimum TENS stimulus intensity." The electrical stimulator 110 may continue to generate pulses of increasing amplitude (or of any variation in the electrical pulse characteristics) until EMG unit 130 detects an M-wave. Stimulus level which leads to the generation of the first M-wave will be recorded as the "Maximum TENS stimulus intensity."

Responsive to scanning for H-reflex and M-wave, electrical stimulator unit 110 may generate pulses of increasing amplitude (or of any variation in the electrical pulse characteristics) until electromyography sensor 130 detects an H-reflex and M-wave. The first stimulus level leading to the detection of the M-wave will be recorded as the "Minimum optimal contraction stimulus intensity". The electrical stimulator 110 may continue to generate pulses of increasing amplitude (or any variation in the electrical pulse characteristics) until EMG unit 130 detects an M-wave approximately equaling to H-reflex. Stimulus level which leads to the generation of an M-wave approximately equal to an H-reflex will be recorded as the "Maximum optimal contraction stimulus intensity".

Responsive to scanning for H-reflex and M-wave, electrical stimulator unit 110 may generate pulses of increasing amplitude (or of any variation in the electrical pulse characteristics) until electromyography sensor 130 detects an H-reflex approximately equal to an M-wave. The first stimulus level which leads to the generation of an M-wave approximately equal to an H-reflex will be recorded as the "Start of Maximal contraction stimulus intensity".

Responsive to scanning for H-reflex and M-wave, if no measurable signal was recorded (either H-reflex, or M-wave), the control unit stops generating pulses of increasing amplitude after reaching a preset maximum amplitude level. The initial pulse amplitude limit could be set at around 20V or any value between 0 V and 50 V.

Figure 2:
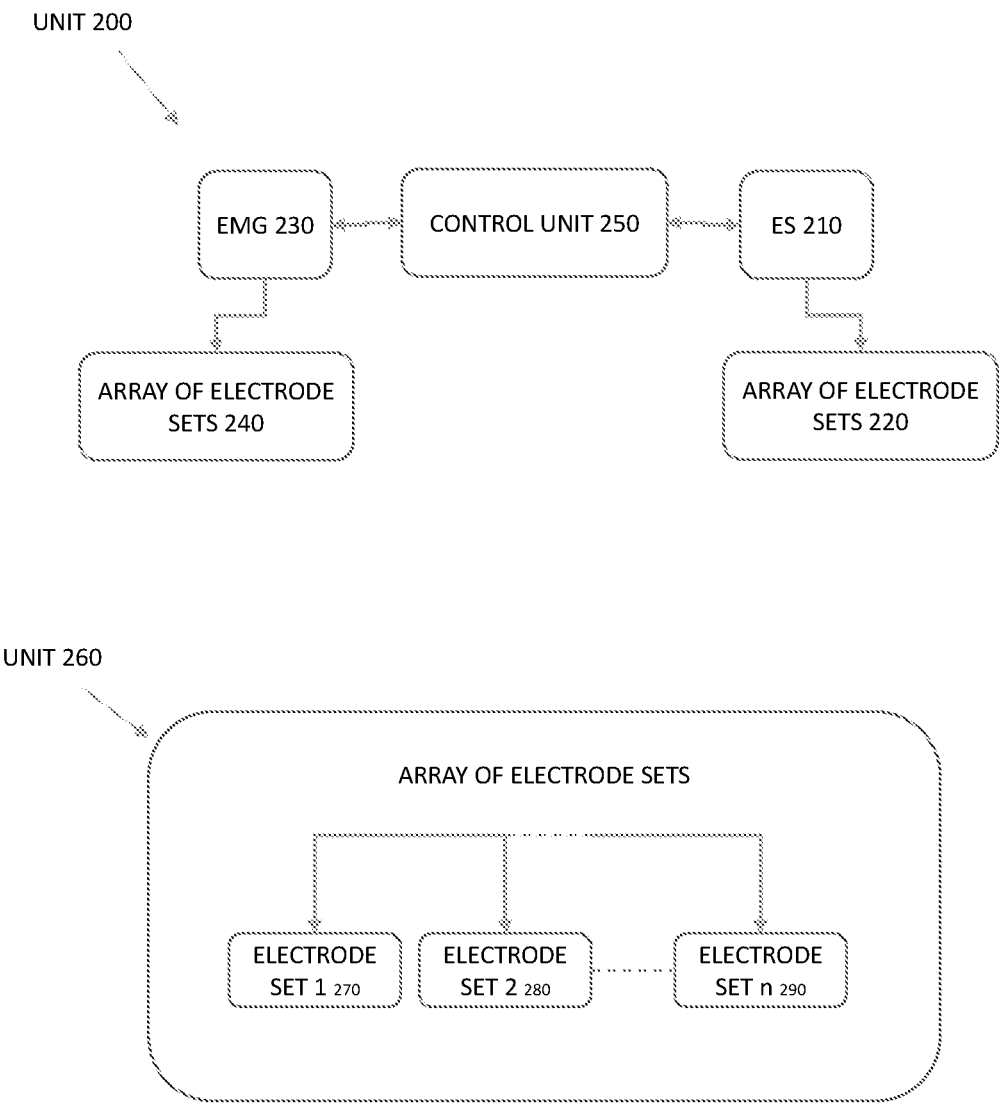
FIG. 2 depicts a wearable or non-wearable device to scan and select an electrode set over a motor point, according to an embodiment.

FIG. 2, depicts a wearable or non-wearable device 200 including an electrical stimulator (ES) 210, first array of electrode sets 220, an electrical measurement system represented as an electromyography (EMG) sensor 230, second array of electrode sets 240, a control unit 250. Unit 260 demonstrates an array of electrode sets containing an n-number of electrodes. Device 200 may be integrated into one enclosure or electronic embodiment. Device 200 may be configured to determine a minimum amplitude range to generate a muscle contraction, and determine the motor point at target muscle organ based on H-reflex and M-wave.

Electrical stimulator 210 may be a device that produces an electrical pulse with characteristics related to current intensities, voltage amplitudes, ramp up/down time, pulse width, pulse frequency, pulse phase, duty cycle, pulse edge slopes (such as rise and fall time), symmetrical or asymmetrical pulses, monophasic or biphasic pulses, or any other characteristics. Electrical stimulator 210 may be configured based on a signal received from the control unit 250 that configures the characteristics of the electrical pulses. In embodiments, electrical stimulator 210 may be configured to generate a low-amplitude-wide-pulse-high-frequency stimulus or any other stimulus to activate an afferent sensory volley or to generate a conventional electrical pulse to activate the motor nerve. Electrical stimulator 210 may be configured to stimulate and generate nerve fibers via array of electrode sets 220, which transmit the generated pulses to the targeted area. In embodiments, electrical stimulator 210 may be configured to transmit the electrical pulses sequentially or simultaneously through first array of electrode sets 220.

First array of electrode sets 220 may be configured to transmit electrical pulses generated by electrical stimulator 210. In embodiments, first array of electrode sets may each include a plurality of electrodes that are each configured to independently and/or simultaneously transmit electrical pulses or waveforms. In embodiments, different electrode sets within the first array of electrode sets may be activated independently or simultaneously.

Electromyography sensor 230 may be a device that is configured to detect the electrical potential generated by muscle cells when these cells are electrically or voluntarily activated. Electromyography sensor 230 may be coupled with a plurality of second array of electrode sets 240 that are spread and placed over muscle mass on multiple locations. Electrical stimulator 210 may sweep the stimulation by varying the electrical pulse characteristics such as increasing the stimulus intensity until electromyography sensor 230 detects, via second array of electrode sets 240 (or same array of electrode sets), an effective response from the target muscle or organ. When an effective response from the target muscle is detected, control unit 250 may be configured to save the detected data associated with the corresponding transmitted stimulus generated by electrical stimulator that caused the effective response from the target muscle.

In embodiments, electromyography sensor 230 may be configured based on a signal received from control unit 250 to determine electrical muscle activity at a predetermined time delay after the pulse stimulus is transmitted from electrical stimulator 210. The predetermined delay of the muscle activity may be around 5 ms or around 25 ms (or any variation of this time), wherein an H-reflex value may be determined around 25 ms after the transmitted stimulus from electrical stimulator 210 and an M-wave may be determined around 5 ms after the transmitted stimulus from electrical stimulator 210. For example, at low intensity, electromyography sensor 230 may determine an H-reflex at 25 ms after the stimulus is transmitted from electrical stimulator 210 via first array of electrode sets 220.

Second array of electrode sets 240 may be configured to determine data associated with muscle response to stimulus transmitted via first array of electrode sets 220, such as data associated with an H-reflex and/or an M-wave. Second array of electrode sets 240 may include a plurality of electrodes that are each configured to independently or simultaneously sense muscle reaction, wherein second array of electrode sets 240 may be positioned at various locations on the skin of a user. For example, second array of electrode sets 240 may be positioned over muscle belly. Array of electrode sets 240 and array of electrode sets 220 could be joined in one single unit or could be two independent units.

In embodiments, the positioning of second array of electrode sets 240 may be proximate to the positioning of first array of electrode sets 220, wherein first array of electrode sets 220 may transmit a pulse or waveform onto the targeted area of a user and second array of electrode sets 240 may receive the bioelectrical feedback caused by the transmitted stimulus. First array of electrode sets 220 and second array of electrode sets 240 could be embedded into one unit or could be separated into two units. In a different embodiment, the array of electrode sets may be configured to transmit pulses or waveforms onto a targeted area on a user then switch in function to sense bioelectrical feedback (the same electrodes have ES and EMG functions).

Unit 260 demonstrates an array of electrode sets that may be composed of an n-number of electrode sets, where "n" could represent a pair number or an odd number of electrode sets. Unit 260 could be configured to operate as stimulating electrodes, sensing electrodes, or could be configured to operate as stimulating electrodes then switch in function to sensing electrodes. Electrode sets 270, 280, and 290 may represent an n-number of electrode sets built into the array of electrode sets 240 and 220. An Electrode set, 270, 280, or 290 within an array of electrode sets may be individually selected to transmit electrical stimulus generated by electrical stimulator 210 or individually selected to measure a bioelectrical feedback using EMG 230.

Control unit 250 may be a hardware processing device configured to control electrical stimulator (ES) 210 and electromyography sensor 230. Control unit 250 may include a processing device and memory. The processing device can include memory, e.g., read only memory (ROM) and random access memory (RAM), storing processor-executable instructions and one or more processors that execute the processor-executable instructions. In embodiments where the processing device includes two or more processors, the processors may operate in a parallel or distributed manner.

The memory device may be a device configured to store data generated or received by control unit 250. The memory device may include, but is not limited to a hard disc drive, an optical disc drive, and/or a flash memory drive.

In embodiments, control unit 250 may be able to control the entirety of the pulse characteristics including but not limited to current intensities, voltage amplitudes, ramp up/down time, pulse width, pulse frequency, pulse phase, duty cycle, pulse edge slopes (such as rise and fall time), symmetrical or asymmetrical pulses, monophasic or biphasic pulses transmitted by electrical stimulator 210. Additionally, control unit 250 may be configured to determine the preset time delay since when the stimulus generated by the electrical stimulator 210 is transmitted until when electromyography sensor 230 detects and read the muscle response as reflected by an H-reflex or M-wave.

Responsive to detecting an H-reflex and/or M-wave at a minimal stimulus intensity, control unit 250 may be programmed to identify the electrode set positioned over the motor point or in near proximity to the motor point. The H-reflex generated by applying the minimal electrical stimulus via a selected stimulation electrode set is called "H-reflex minimum." The associated electrode set that caused "H-reflex minimum" is labeled as the "H-reflex minimum electrode set." The M-wave generated by applying the minimal electrical stimulus via a selected stimulation electrode set is called "M-wave minimum." The associated electrode set that caused "M-wave minimum" is labeled as the "M-wave minimum electrode set." Once an "H-reflex minimum" is detected by the EMG unit 230, the electrode set labeled as the "H-reflex minimum electrode set" will be identified as the electrode set positioned near or over a motor point. If no H-reflex detected and only an "M-wave minimum" was detected by the EMG unit 230, the electrode set labeled as the "M-wave minimum electrode set" will be identified as the electrode set positioned near or over a motor point. If both "H-reflex minimum" and "M-wave minimum" detected by the EMG unit 230 at similar stimulus intensity levels, then the electrode set labeled as the "M-wave minimum electrode set" will be identified as the electrode set positioned near or over a motor point. If "H-reflex minimum" and "M-wave minimum" were not detected by EMG unit 230 then the device may determine that no electrode sets can be identified to be near or over a motor point.

A motor point identification may be possible once the minimal stimulus intensity values needed to generate H-reflex and/or M-wave are determined for each electrode set within the array of electrode sets 220. The control unit 250 may determine the lowest stimulation intensity associated with each "H-reflex minimum" and/or "M-wave minimum". Control unit 250 may then designate the electrode set associated with the lowest stimulus intensity which caused the maximum amplitude of "H-reflex minimum" as the "H-reflex minimum electrode set". The "H-reflex minimum electrode set" may be designated as the primary electrode set located over or in near proximity to a motor point. In case an H-reflex is not detected and an M-wave is detected, the electrode set associated with the lowest stimulus intensity which caused the maximum amplitude of "M-wave minimum" may be designated as the "M-wave minimum electrode set." The "M-wave minimum electrode set" may be designated as the primary electrode set located over or in near proximity to a motor point. If both "H-reflex minimum" and "M-wave minimum" are detected at similar stimulus intensity levels, then control unit may compare the values of "M-wave minimum", the electrode set associated with the lowest stimulus intensity which caused the maximum amplitude of "M-wave minimum" may be designated as the "M-wave minimum electrode set". The "M-wave minimum electrode set" may be designated as the primary electrode set located over or in near proximity to a motor point. If "H-reflex minimum" and "M-wave minimum" were not detected by EMG unit 230 then the device may determine that no electrode sets can be identified to be over or in near proximity to a motor point.

Figure 3:
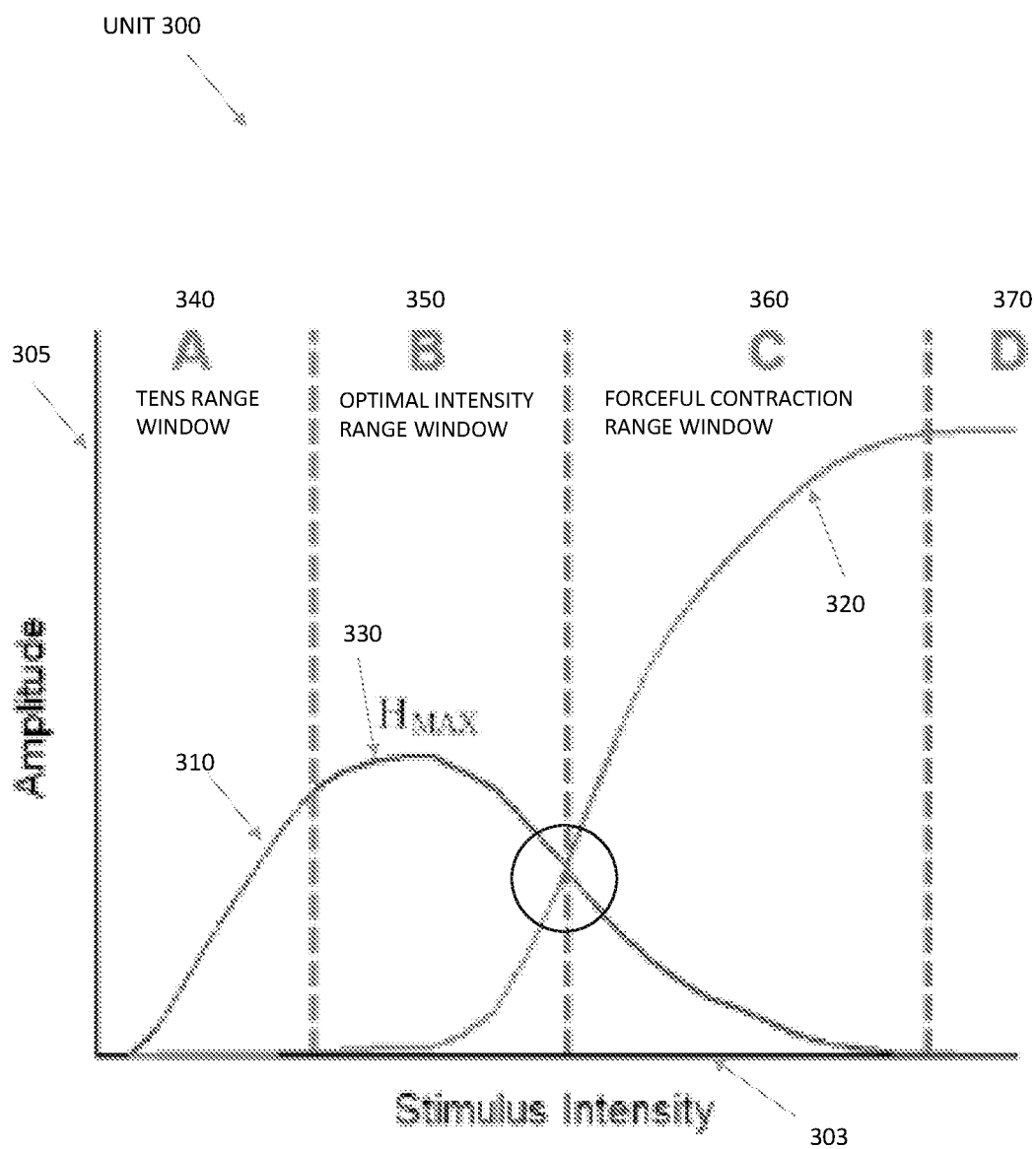
FIG. 3 depicts a graph showing the different stimulation range windows in function of H-reflex values and M-wave values for different stimulus intensities, according to an embodiment.

FIG. 3 depicts a graph 300 including H-reflex values 310 and M-wave values 320 with the therapeutic window ranges in function of the stimulus intensity. According to an embodiment. Graph 300 may be associated with a first electrode set transmitting stimulus and a second electrode set sensing bioelectrical feedback. Graph 300 has an x-axis 303 indicating stimulus strength of the pulse or wave form applied by electrical stimulator 110 or 210, and a y-axis 305 indicating response amplitude measured by electromyography sensor 130 or 230. The H-reflex values 310 may be generated by applying electrical stimulation to an afferent sensory Ia axon fiber. The M-wave values 320 may be generated by efferent motor axon simulation.

As depicted in FIG. 3, as the stimulus strength increases the response amplitude of the H-reflex value may increase to a maximum 330 H-reflex value. After the maximum 330 H-reflex value, increasing stimulus amplitude may decrease the response amplitude associated with the H-reflex values 310.

As further depicted in FIG. 3, the stimulus amplitude required to generate H-reflex values 310 may be less than the stimulus amplitude required to generate an M-wave 320. This may occur because the M-wave physiological threshold is higher than the H-reflex physiological threshold.

Not illustrated in FIG. 3, the occurrence time of the H-reflex may have a slight time delay from the occurrence time of the M-wave (M-wave occurs earlier in time in comparison with H-reflex: approximately 5 ms vs 25 ms after stimulus is transmitted, respectively).

At a given first intensity range 340, EMG unit 130 will detect an H-reflex and no significant M-wave values. This corresponds to "TENS range window" ("Phase A" of FIG. 3). A second intensity range 350 is determined for an increased stimulus intensity compared to the first intensity range. In the second intensity range 350, the amplitude of H-reflex values 310 are larger than the amplitude of M-wave 320 values. This corresponds to "Optimal intensity range window" ("Phase B" of FIG. 3). With further increase in stimulus intensity compared to the first and second intensity ranges, a third intensity range 360 is determined, the amplitude of H-reflex values 310 will be lower than the amplitude of M-wave values 320. This corresponds to "Forceful contraction range window" ("Phase C" of FIG. 3). With further increase in stimulus intensity and in a fourth intensity range 370, there may no longer be a detectable amplitude of H-reflex values 310, and the amplitude of M-wave values 320 may plateau.

Figure 4:
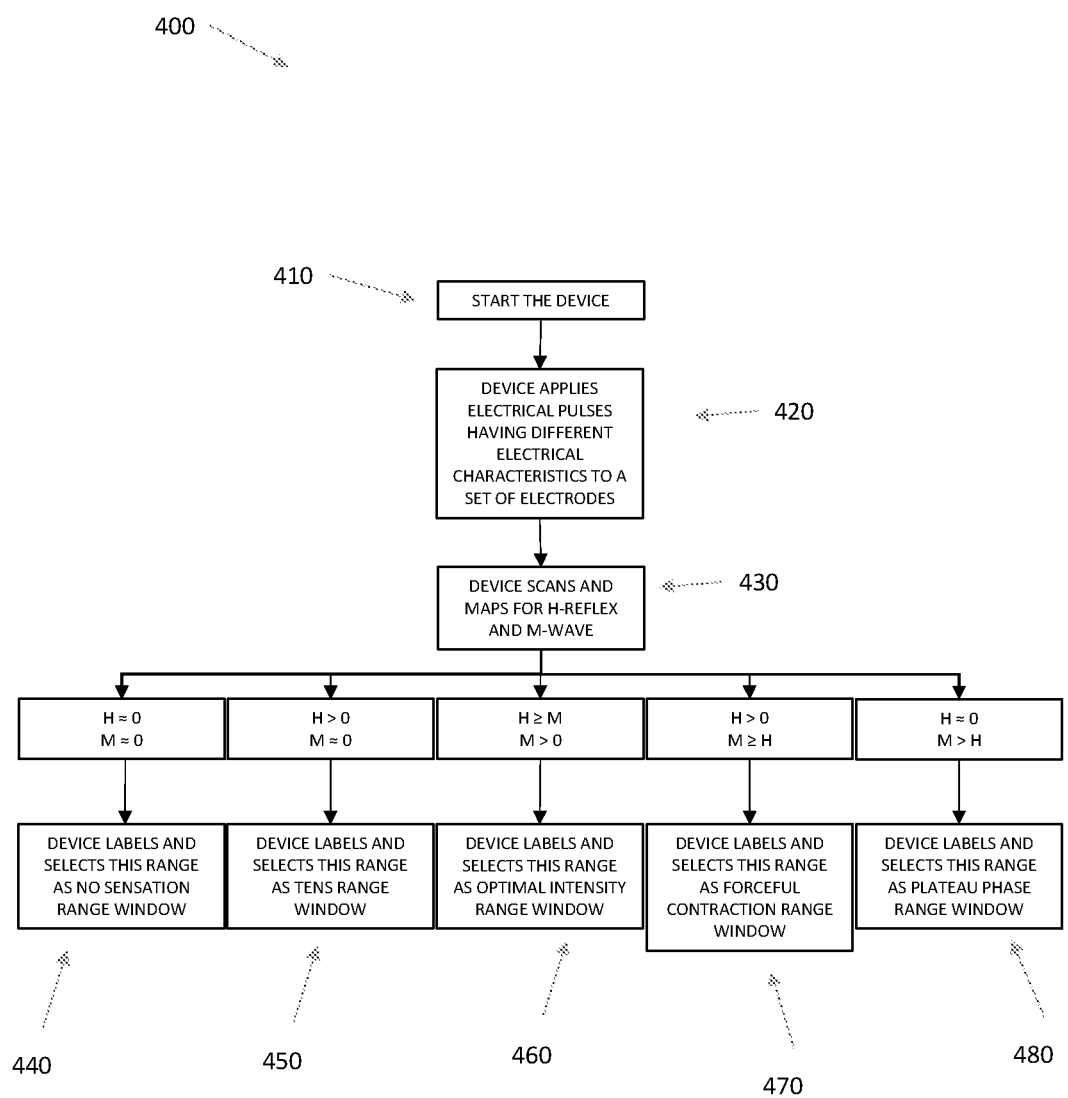
FIG. 4 depicts a method for utilizing a wearable and/or non-wearable device including an electrical stimulator (ES), first set of stimulating electrodes, an electrical measurement system such as an electromyography sensor, second set of sensing electrodes, and a control unit to determine a stimulus intensity range, according to an embodiment.
Figure 7:
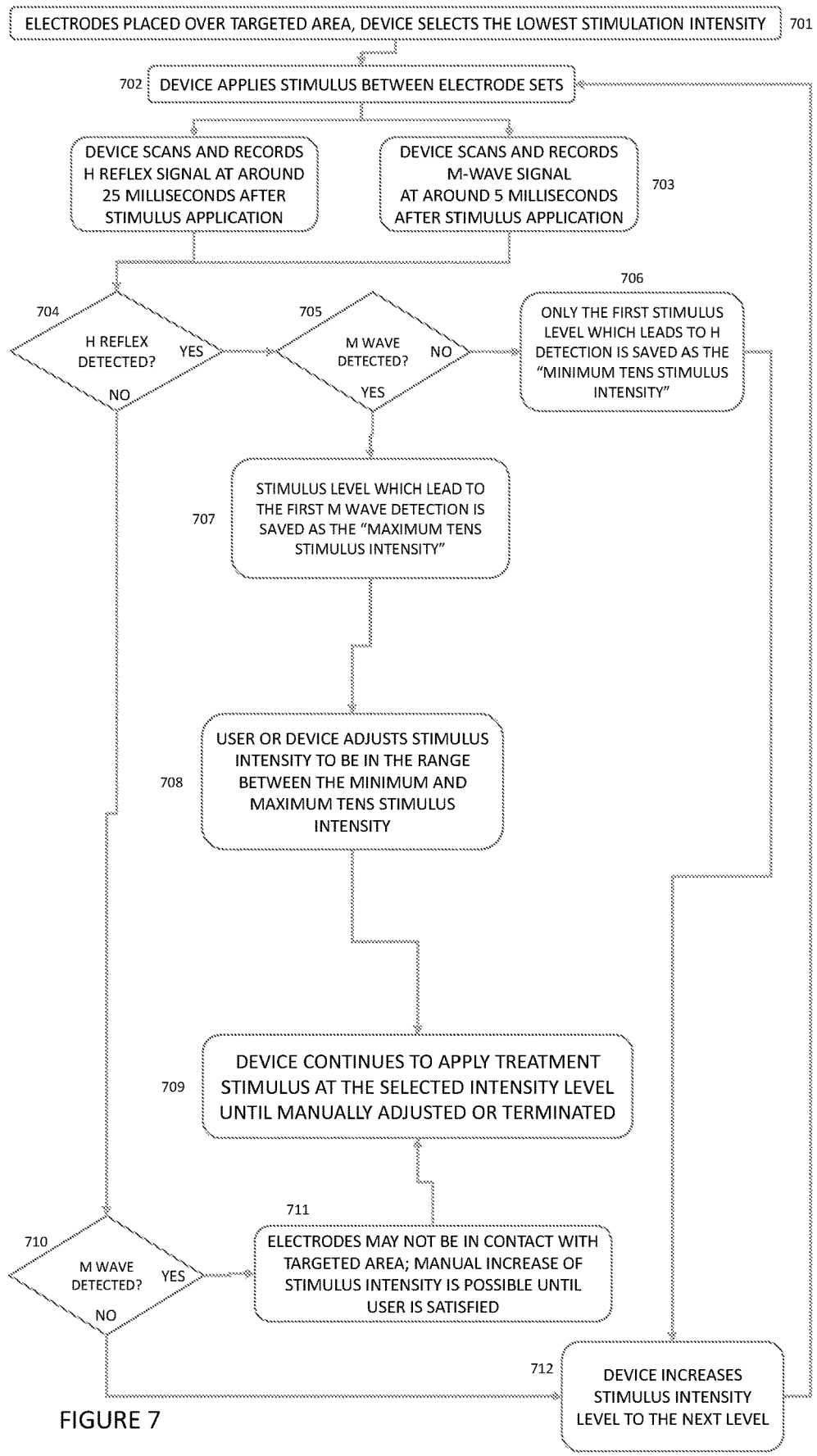
FIG. 7, FIG. 8, and FIG. 9, depict methods for a system as illustrated in FIG. 4 above, wherein FIGS. 7 to 9 demonstrate potential algorithms for detecting the different amplitude ranges, according to an embodiment.
Figure 8:
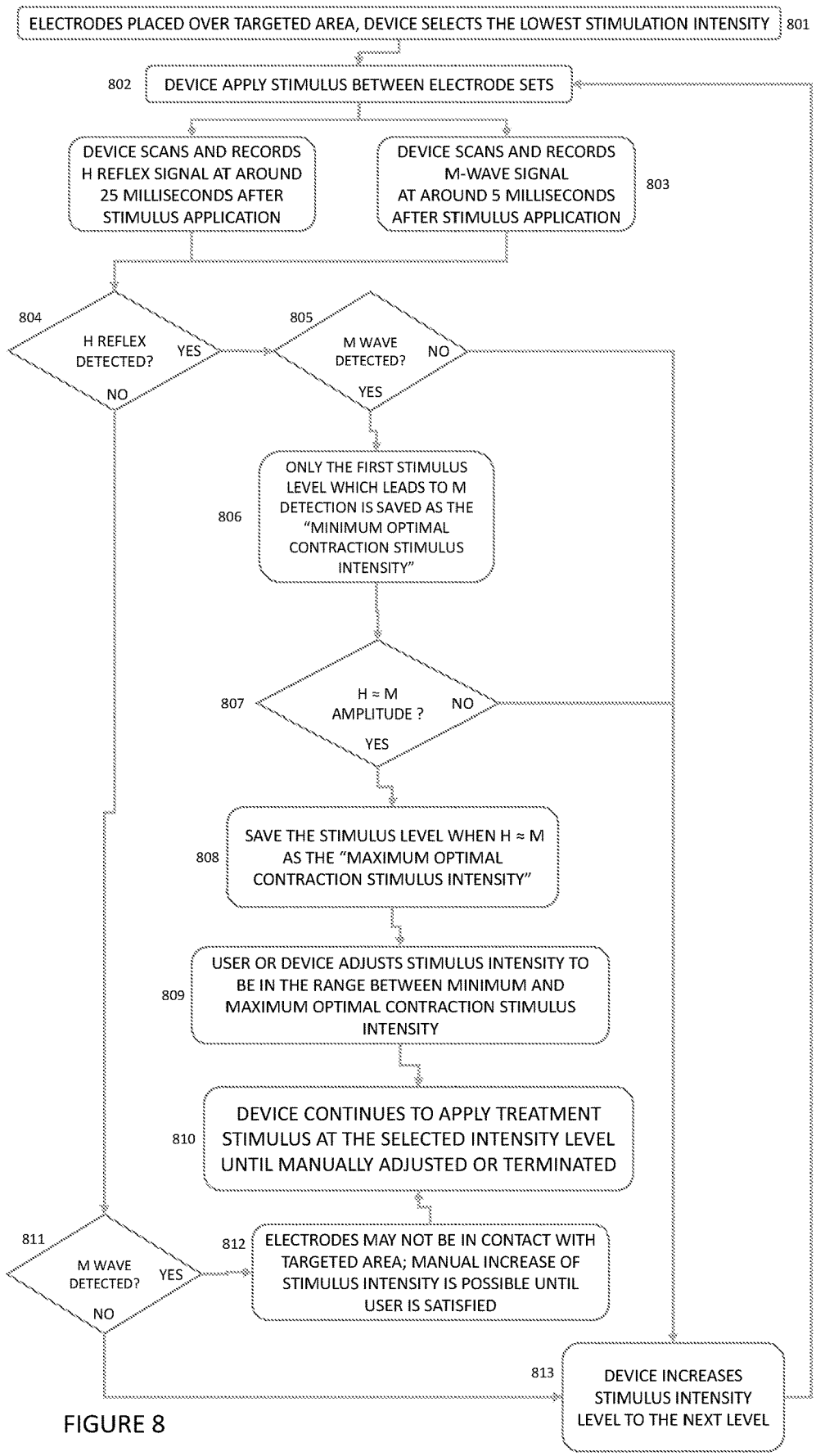
Figure 9:
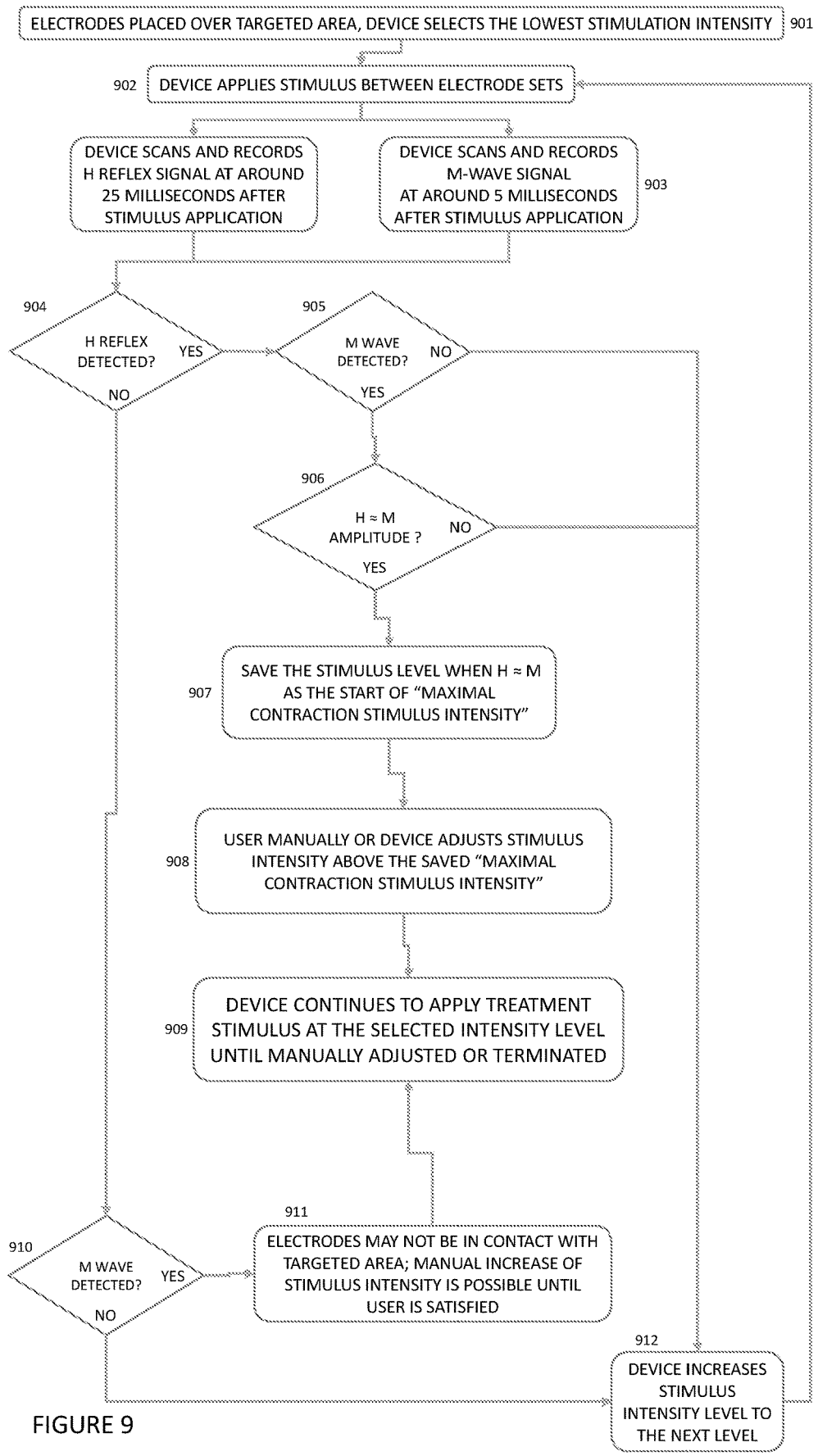

FIG. 4 depicts a method 400 for utilizing a wearable and/or non-wearable device 100 including an electrical stimulator (ES), first electrode set, electromyography sensor, second electrode set, and a control unit to determine the effective intensity range level. The operations of methods presented below are intended to be illustrative. In some embodiments, the methods may be accomplished with one or more additional operations not described, and/or without one or more of the operations discussed. Additionally, the order in which the operations of the methods are illustrated in FIG. 4 depicts and described below is not intended to be limiting. FIG. 7, FIG. 8, and FIG. 9 illustrate a potential detailed approach to determining the different intensity ranges.

At operation 410, user starts the device.

At operation 420, device applies electrical pulses having different electrical characteristics to a set of electrodes.

At operation 430, device scans and maps H-reflex and M-wave in function of electrical pulse characteristics.

At operation 430, the control unit may determine and record H-reflex signal data at around 25 ms after stimulus is applied. Furthermore, the control unit may determine and record M-wave signal data at around 5 ms after stimulus is applied.

At operation 430, device may repeat operation 420 while increasing the electrical stimulus intensity. This process may be repeated until mapping the H-reflex value and M-wave value as follow:

At operation 440, control unit 150 detects H-reflex and M-wave. If H-reflex and M-wave values are of negligible significance, device labels the intensity range as "No sensation Range" window.

At operation 450, control unit 150 detects H-reflex and M-wave. If H-reflex>0 and M-wave value is of negligible significance, the stimulation range is entitled "TENS Range" window.

At operation 460, control unit 150 detects H-reflex and M-wave. If H-reflex≥M-wave and M-wave>0, the stimulation range is entitled "Optimal intensity range" window.

At operation 470, control unit 150 detects H-reflex and M-wave. If H-reflex>0 and M-wave≥H-reflex, the stimulation range is entitled "Forceful contraction range" window.

At operation 480, control unit 150 detects H-reflex and M-wave. If H-reflex value is of negligible significance and M wave>H, the stimulation range is entitled "plateau phase range" window.

Device may continuously control and regulate stimulus intensity level according to selected stimulation range window by continuously monitoring H-reflex and M-wave while adjusting stimulus intensity level to meet the ranges defined at operation 440-480.

Figure 5:
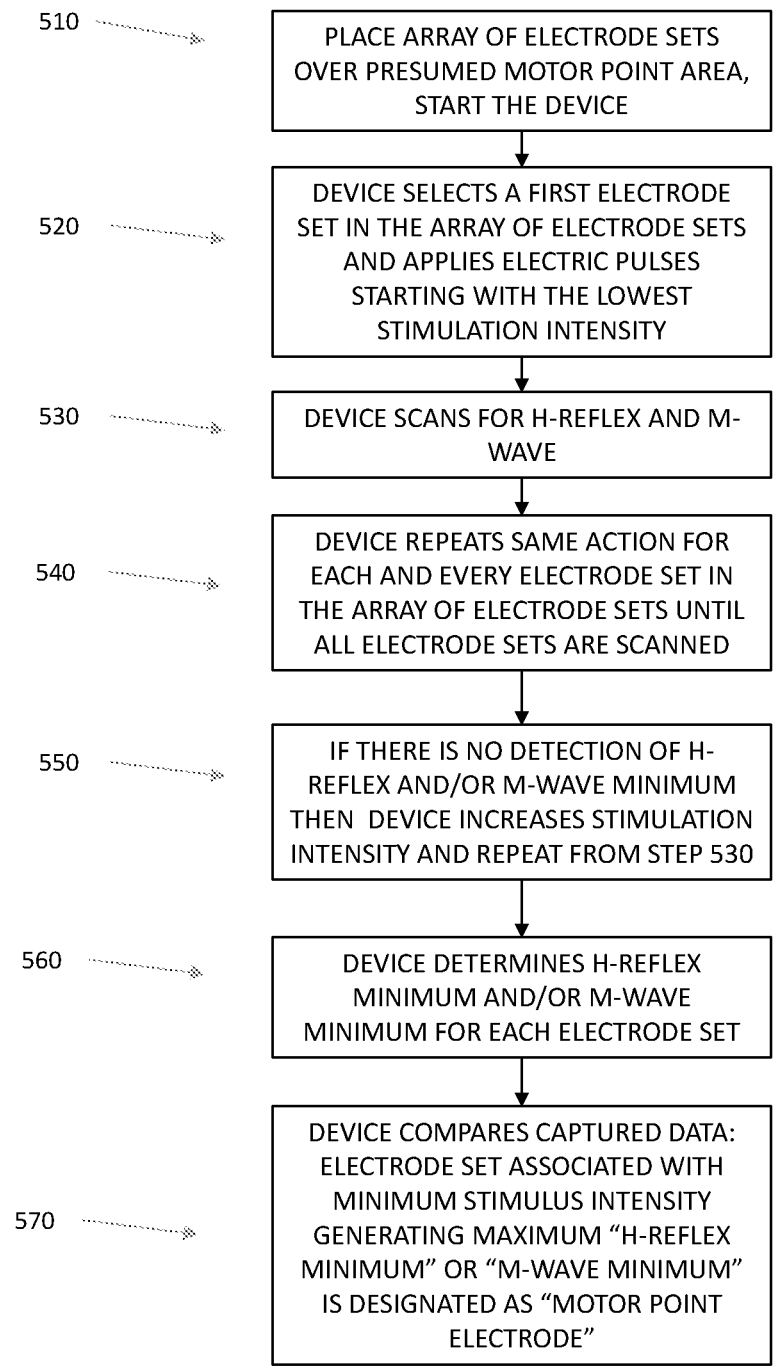
FIG. 5 depicts a method for utilizing a wearable and/or non-wearable device including an electrical stimulator (ES), first array of stimulating electrode sets, an electrical measurement system such as an electromyography sensor, second array of sensing electrode sets, and a control unit to determine a motor point location, according to an embodiment.
Figure 6:
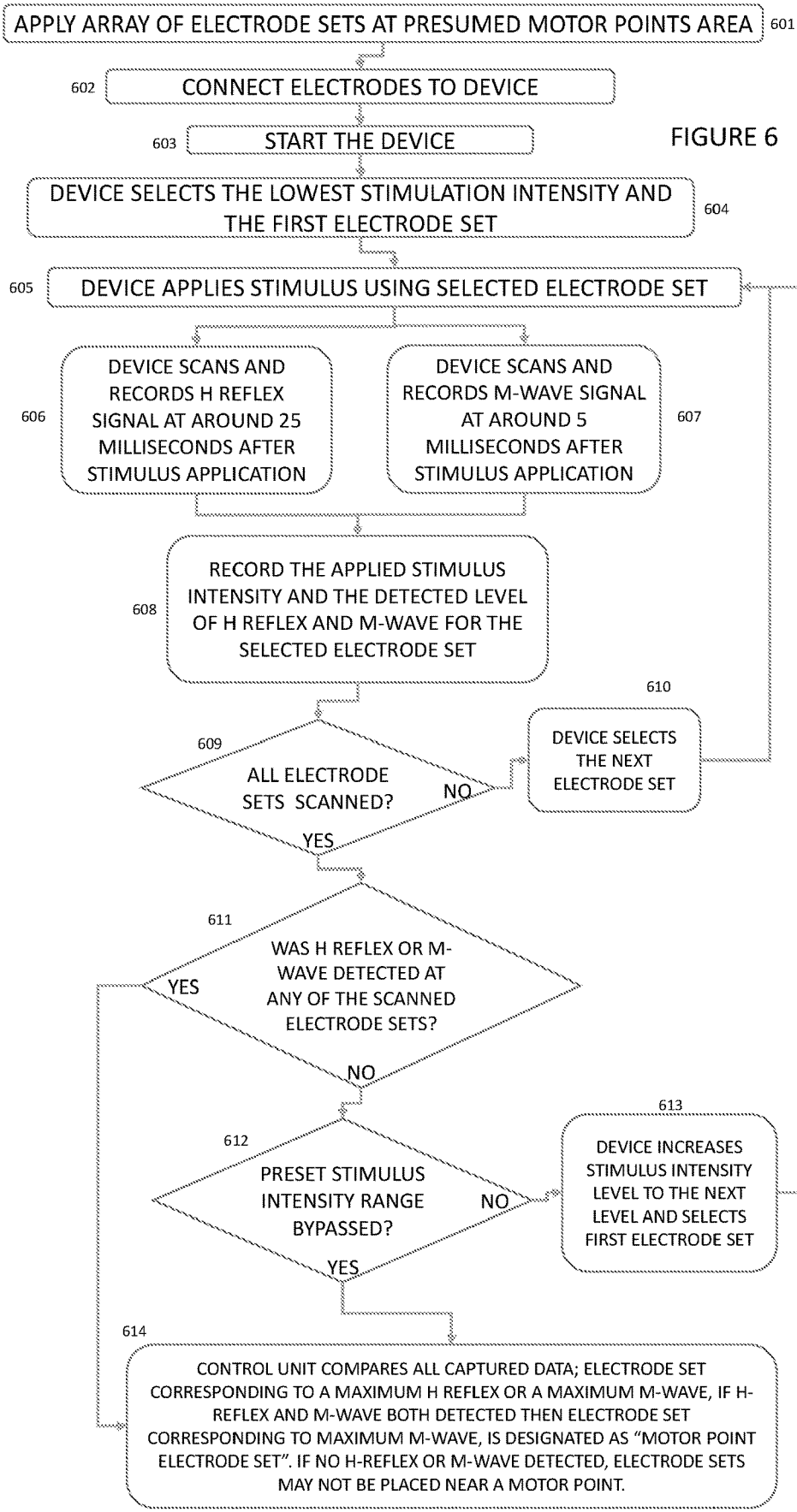
FIG. 6 depicts a method for a system to detect Motor point as illustrated in FIG. 5 above, wherein FIG. 6 demonstrates one potential algorithm to detect the motor point, according to an embodiment.

FIG. 5 depicts a method 500 for a system to determine a motor point location, according to an embodiment. The operations of methods presented below are intended to be illustrative. In some embodiments, the methods may be accomplished with one or more additional operations not described, and/or without one or more of the operations discussed. Additionally, the order in which the operations of the methods are illustrated in FIG. 5 depicts and described below is not intended to be limiting. FIG. 6 illustrates one potential approach to determining the motor point location.

At operation 510, user places array of electrode sets over presumed motor point area and starts the device.

At operation 520, device selects a first electrode set in the array of electrode sets and applies electrical pulses starting with the lowest stimulation intensity.

At operation 530, device scans for H-reflex and M-wave.

At operation 530, the control unit scans for an H-reflex signal at around 25 ms after a stimulus is applied to an electrode set. Furthermore, the control unit scans for an M-wave signal at around 5 ms after stimulus is applied to an electrode set.

At operation 540, the device repeats the previous scan operation for each and every electrode set in the array of electrode sets until all electrode sets are scanned.

At operation 550, if H-reflex minimum or M-wave minimum are not detected then device increases stimulation intensity and restarts from step 530.

At operation 560, the device determines H-reflex minimum and/or M-wave minimum for each electrode set.

At operation 570, the device compares the captured data. The electrode set associated with the minimum stimulus intensity generating Maximum "H-reflex minimum" or "M-wave minimum" is designated as "Motor Point Electrode set". The "Motor Point Electrode set" may be mainly selected by the device to deliver efficient electrical stimulation to the user.

FIG. 6 illustrates a method for utilizing a wearable and/or non-wearable device 200 including an electrical stimulator (ES) 210, first array of electrode sets 220, electromyography sensor 230, second array of electrode sets 240, and a control unit 250. The operations of methods presented below are intended to be illustrative. In some embodiments, the methods may be accomplished with one or more additional operations not described, and/or without one or more of the operations discussed. Additionally, the order in which the operations of the methods are illustrated in FIG. 6 depicts and described below is not intended to be limiting. The diagrams' logic described below could be used independently or sequentially.

Diagram 6 Motor Point Identification:

1. At operation 601, apply array of electrode sets at presumed motor point area.
2. At operation 602, connect electrodes to device.
3. At operation 603, start the device.
4. At operation 604, device selects the lowest stimulation intensity and the first electrode set.
5. At operation 605, device applies stimulus using selected electrode set.
6. At operation 606, device scans and records H-reflex signal at around 25 ms after stimulus application. Execution jumps to operation 608.
7. At operation 607, device scans and records M-wave signal at around 5 ms after stimulus application. Execution jumps to operation 608.
8. At operation 608, device records the applied stimulus intensity and the detected or measured level of H-reflex and M-wave for the selected electrode set.
9. At operation 609, device checks if all electrode sets were scanned:
   If "no" then execution jumps to operation 610
   if "yes" then execution jumps to operation 611
10. At operation 610, device selects the next electrode set that was not previously selected within the array then jumps to operation 605.
11. At operation 611, device checks if H-reflex or M-wave were detected at any of the scanned electrode sets:
    If "no" then execution jumps to operation 612
    if "yes" then execution jumps to operation 614
12. At operation 612, device checks if preset stimulus intensity range was bypassed:
    If "no" then execution jumps to operation 613
    If "yes" then execution jumps to operation 614
13. At operation 613, device increases stimulus intensity level to the next level and selects first electrode set then jump to operation 605.
14. At operation 614, control unit 250 compares all captured data. Electrode set corresponding to maximum amplitude of "H-reflex minimum" caused by the minimum stimulus intensity is designated as "Motor point electrode set". If H-reflex was not detected then control unit 250 scans for "M-wave minimum" caused by the minimum stimulus intensity. Electrode set corresponding to maximum amplitude of "M-wave minimum" caused by the minimum stimulus intensity is designated as "Motor point electrode set". If both "H-reflex minimum" and "M-wave minimum" are detected at similar stimulus intensity levels, then electrode set corresponding to maximum amplitude of "M-wave minimum" caused by the minimum stimulus intensity is designated as "Motor point electrode set". Device may continuously select the electrode set designated as motor point electrode set to deliver an effective electrical stimulation to the user. If H-reflex and M-wave are not detected, the device may determine that electrode sets may not be placed over or in near proximity of the motor point.

FIGS. 7 to 9 illustrate methods for utilizing a wearable and/or non-wearable device 100 including an electrical stimulator (ES) 110, first electrode set 140, electromyography sensor 130, second electrode set 140, and a control unit 150. The operations of methods presented below are intended to be illustrative. In some embodiments, the methods may be accomplished with one or more additional operations not described, and/or without one or more of the operations discussed. Additionally, the order in which the operations of the methods are illustrated in FIGS. 7 to 9 depicts and described below is not intended to be limiting. The FIGURES' logic described below could be used independently or sequentially.

FIG. 7 TENS range window:
1. At operation 701, electrode sets are placed over targeted area. The device selects the lowest stimulation intensity.
2. At operation 702, device applies stimulus between electrode sets.
3. At operation 703, the device scans and records H-reflex and M-wave at around 25 ms and 5 ms respectively.
4. At operation 704, device checks if H-reflex was detected:
   If "yes" then execution jumps to operation 705
   If "no" then execution jumps to operation 710
5. At operation 705, device checks if M-wave was detected:
   If "no" then execution jumps to operation 706
   If "yes" then execution jumps to operation 707
6. At operation 706, the device records the first stimulus level resulting in the detection of an H-reflex as the "Minimum TENS stimulus intensity". Execution jumps to operation 712.
7. At operation 707, the device records the stimulus level resulting in the detection of the first M-wave as the "Maximum TENS stimulation intensity". Execution jumps to operation 708.
8. At operation 708, the user manually, or the device automatically adjusts the stimulus amplitude range between the "Minimum and Maximum TENS stimulus intensity". Execution jumps to operation 709.
9. At operation 709, the device continues to apply treatment stimulus at the selected intensity level until manually adjusted or terminated.
10. At operation 710, device checks if M-wave was detected:
    If "yes" then execution jumps to operation 711
    If "no" then execution jumps to operation 712
11. At operation 711, the device may determine that the electrode sets may not be in contact with "Targeted Area". User may manually control the amplitude level.
12. At operation 712, device increases stimulus intensity level to the next level.

FIG. 8 Optimal intensity range window:
1. At operation 801, electrode sets are placed over targeted area. The device selects the lowest stimulation intensity.
2. At operation 802, device applies stimulus between electrode sets.
3. At operation 803, the device scans and records H-reflex and M-wave at around 25 ms and 5 ms respectively.
4. At operation 804, device checks if H-reflex was detected:
   If "yes" then execution jumps to operation 805
   If "no" then execution jumps to operation 811
5. At operation 805, device checks if M-wave was detected:
   If "yes" then execution jumps to operation 806
   If "no" then execution jumps to operation 813
6. At operation 806, the device records only the first stimulus level resulting in M-wave detection as "Minimum Optimal Contraction Stimulus intensity". Execution jumps to operation 807.
7. At operation 807, device checks if H-reflex amplitude≈M-wave amplitude:
   If "yes" then execution jumps to operation 808
   If "no" then execution jumps to operation 813
8. At operation 808, the device saves the stimulus level when H-reflex amplitude≈M-wave amplitude as the "Maximal optimal contraction stimulus intensity". Execution jumps to operation 809.
9. At operation 809, the user manually, or the device automatically adjusts stimulus intensity to be in the range between "Minimum and Maximum optimal contraction stimulus intensity".
10. At operation 810, device continues to apply treatment stimulus at the selected intensity level until manually adjusted or terminated.
11. At operation 811, device checks if M-wave was detected:
    If "yes" then execution jumps to operation 812
    If "no" then execution jumps to operation 813
12. At operation 812, the device may determine that the electrode sets may not be in contact with "Targeted Area". User may manually control the stimulus intensity level.
13. At operation 813 device increases stimulus intensity level to the next level.

FIG. 9 Forceful contraction range window:
1. At operation 901, electrode sets are placed over targeted area, the device selects the lowest stimulation intensity.
2. At operation 902, device applies stimulus between electrode sets.
3. At operation 903, the device scans and records H-reflex and M-wave at around 25 ms and 5 ms respectively. Execution jumps to operation 904.
4. At operation 904, device checks if H-reflex was detected:
   If "yes" then execution jumps to operation 905
   If "no" then execution jumps to operation 910
5. At operation 905, device checks if M-wave was detected:
   If "yes" then execution jumps to operation 906
   If "no" then execution jumps to operation 912
6. At operation 906, device checks if H-reflex amplitude≈M-wave amplitude:
   If "yes" then execution jumps to operation 907
   If "no" then execution jumps to operation 912
7. At operation 907, the device saves the stimulus level when H-reflex amplitude≈M-wave amplitude as the "Start of Maximal contraction stimulus intensity". Execution jumps to operation 908.
8. At operation 908 user manually, or the device automatically adjusts stimulus intensity above the saved "Maximal contraction stimulus intensity". Execution jumps to operation 909.
9. At operation 909, device continues to apply treatment stimulus at the selected intensity level until manually adjusted or terminated.
10. At operation 910, device checks if M-wave was detected:
    If "yes" then execution jumps to operation 911
    If "no" then execution jumps to operation 912
11. At operation 911, the device may determine that the electrode sets may not be in contact with "Targeted Area". User may manually control the stimulus intensity level.
12. At operation 912 device increases stimulus intensity level to the next level.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

What is claimed is:

1. A system for determining a stimulus range to cause different physiological responses varying from local tingling sensation to muscle contraction, the system comprising:
    an electrical stimulator configured to produce electrical pulse stimulus;
    a first set of electrodes configured to transmit to a user a range of electrical pulse stimulus generated by the electrical stimulator including a first electrical pulse stimulus,
    an electrical measurement system configured to detect bioelectrical feedback in response to the first electrical pulse stimulus generated by the electrical stimulator,
    a second set of electrodes configured to receive from the user the bioelectrical feedback in response to the first electrical pulse stimulus generated by the electrical stimulator,
    a controller unit system to automatically control and regulate the electrical stimulator providing the electrical pulse stimulus to the first set of electrodes based on the bioelectrical feedback caused by the first electrical pulse stimulus, the bioelectrical feedback including an H-reflex and a M-wave, wherein the controller unit varies pulse amplitude and time characteristics of the electrical pulse stimulus until an electromyography sensor detects a ratio approximately equal to one between amplitudes of an H-reflex signal of the H-reflex at a first predetermined time delay window from the first electrical pulse stimulus and of an M-wave signal of the M-wave at a second predetermined time delay window from the first electrical pulse stimulus.

2. The system of claim 1, wherein the first or second set of electrodes is a cutaneous set of electrode patches.

3. The system of claim 1, wherein the electrical stimulator is configured to generate electrical pulse stimulus with different characteristics.

4. The system of claim 1, the first predetermined time delay window associated with the first electrical pulse stimulus is at around 25 milliseconds after the first electrical pulse stimulus is transmitted and the second predetermined time delay window associated with the first electrical pulse stimulus is at around 5 milliseconds after the first electrical pulse stimulus is transmitted.

5. The system of claim 1, wherein the controller unit system is configured for the user to readjust characteristics of the electrical pulse based on user input.

6. The system of claim 1, wherein the controller unit system is configured for the user to select a stimulation range.

7. The system of claim 1, wherein the first and second electrode sets are built into an array of multitude set of electrodes spread over a surface area.

* * * * *